(12) United States Patent
Peyman et al.

(10) Patent No.: US 6,340,679 B1
(45) Date of Patent: Jan. 22, 2002

(54) GUANIDINE DERIVATIVES AS INHIBITORS OF CELL ADHESION

(75) Inventors: Anuschirwan Peyman, Kelkheim (DE); Jochen Knolle, San Francisco, CA (US); Karl-Heinz Scheunemann, Liederbach (DE); David William Will, Kriftel (DE); Denis Carniato, Marcoussis; Jean-Francois Gourvest, Claye Souilly, both of (FR); Thomas R. Gadek, Oakland; Sarah Catherine Bodary, San Bruno, both of CA (US)

(73) Assignees: Aventis Pharma Deutschland GmbH, Frankfurt (DE); Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/502,577

(22) Filed: Feb. 11, 2000

(30) Foreign Application Priority Data

Feb. 13, 1999 (EP) .............................. 99102916

(51) Int. Cl.$^7$ .................. C07D 239/16; C07D 409/12; A61K 31/505

(52) U.S. Cl. .................. 514/218; 514/183; 514/242; 514/244; 514/252.01; 514/252.02; 514/255.05; 514/275; 514/341; 514/392; 540/553; 544/179; 544/182; 544/185; 544/194; 544/212; 544/238; 544/295; 544/296; 544/297; 548/314.7; 548/327.5; 546/327.5

(58) Field of Search .................. 514/183, 218, 514/242, 244, 252.01, 252.02, 255.05, 275, 341, 392; 540/553; 544/179, 182, 185, 194, 212, 238, 295, 296, 297; 546/274.7; 548/314.7, 327.5

(56) References Cited

U.S. PATENT DOCUMENTS 5,403,836 A  4/1995 Blackburn et al. .......... 614/213

FOREIGN PATENT DOCUMENTS

| EP | 528 586 | 2/1993 |
| EP | 528 587 | 2/1993 |
| EP | 820 991 | 1/1998 |
| EP | 0 933 367 A1 | 8/1999 |
| WO | 94/08577 | 4/1994 |
| WO | 94/12181 | 6/1994 |
| WO | 95/32710 | 12/1995 |
| WO | 96/00574 | 1/1996 |
| WO | 96/00730 | 1/1996 |
| WO | 97/06791 | 2/1997 |
| WO | 97/23451 | 7/1997 |
| WO | 98/00395 | 1/1998 |
| WO | 99/32457 | 7/1999 |
| WO | 99/37621 | 7/1999 |

OTHER PUBLICATIONS

P. C. Brooks et al., "Integrin $\alpha_v\beta_3$ Antagonists Promote Tumor Regression by Inducing Apoptosis of Angiogenic Blood Vessels", Cell, vol. 79, 1994, pp. 1157–1164.

S. L. Brown et al., "Stimulation of migration of human aortic smooth muscle cells by vitronectin: implications for atherosclerosis", Cardiovascular Research, vol. 28, 1994, pp. 1815–1820.

H. Bundgaard, "Novel chemical approaches in prodrug design", Drugs of the Future, vol. 16:5, 1991, pp. 443–458.

L. A. Carpino, "1–Hydroxy–7–azabenzotriazole. An Efficient Peptide Coupling Additive", J. Am. Chem. Soc., vol. 115, 1993, pp. 4397–4398.

C. P. Carron et al., "A Peptidomimetic Antagonist of the Integrin . . . Hypercalcemia of Malignancy", Cancer Research, vol. 58, 1998, pp. 1930–1935.

M. S. Dennis et al., "Platelet glycoprotein IIb–IIa protein antagonists from snake venoms: Evidence for a Family of platelet–aggregation inhibitors", Proc. Natl. Acad. Sci., vol. 87, 1989, pp. 2471–2475.

(List continued on next page.)

Primary Examiner—Mukund J. Shah
Assistant Examiner—Deepak Rao
(74) Attorney, Agent, or Firm—Foley & Lardner

(57) ABSTRACT

The present invention relates to acylguanidine derivatives of the formula I

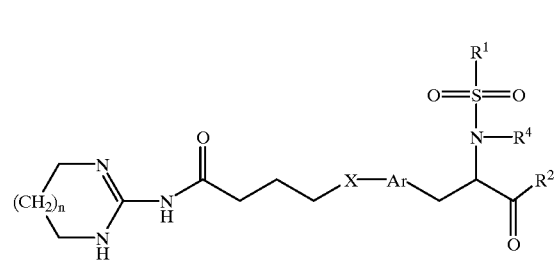

in which $R^1$, $R^2$, $R^4$, Ar, X and n have the meanings indicated in the claims, their physiologically tolerable salts and their prodrugs. The compounds of the formula I are valuable pharmacologically active compounds. They are vitronectin receptor antagonists and inhibitors of cell adhesion. They inhibit, for example, bone resorption by osteoclasts and are suitable for the therapy and prophylaxis of diseases which are caused at least partially by an undesired extent of bone resorption, for example osteoporosis. The invention furthermore relates to processes for the preparation of compounds of the formula I, their use, in particular as active ingredients in pharmaceutical preparations, and pharmaceutical preparations comprising them.

10 Claims, No Drawings

OTHER PUBLICATIONS

M.S. Dennis et al., "Binding Interactions of Kistrin . . . Site Directed Mutagenesis", Proteins: Structure, Function, And Genetics, vol. 15, 1993, pp. 312–321.

V. Wayne Engleman et al., "Cell Adhesion Integrins as Pharmaceutical Targets", Annual Reports in Medicinal Chemistry—Chapter 20, 1996, pp. 191–200.

J. E. Fisher et al., "Inhibition of Osteoclastic Bone Resorption In Vivo by Echistatin, an 'Arginyl–Glycyl–Aspartyl' (RGD)–containing Protein", Endocrinology, vol. 132:3, 1993, pp. 1411–1413.

David Fleisher et al., "Improved oral drug delivery: solubility limitations overcome by the use of prodrugs", Advanced Drug Delivery Reviews, vol. 19, 1996, pp. 115–130.

M. Friedlander et al., "Definition of Two Angiogenic Pathways by District $\alpha_v$ Integrins", Science, vol. 270, 1995, pp. 1500–1502.

G. S. Hillis et al., "Integrins and disease", Clinical Science, vol. 91, 1996, pp. 639–650.

M. A. Horton et al., "Arg–Gly–Asp (RGD) Peptides and the Anti–Vitronectin . . . Cell Spreading by Osteoclasts", Experimental Cell Research, vol. 195, 1991, pp. 368–375.

P. D. Jardine & D. Thompson, "Chapter 22. Anti–Osteoporosis Agents", Annual Reports in Medical Chemistry—31, 1998, pp. 211–220.

W. König et al., "Perchloric acid in peptide chemistry", Peptides, 1990, pp. 143–145.

P. J. Newman et al., "Quantitation of Membrane Glycoprotein IIIa on Intact Human Platelets Using the Monoclonal Antibody, AP–3", Blood, vol. 65:1, 1985, pp. 227–232.

M. Safadi et al., "Phosphoryloxymethyl Carbamates and Carbonates—Novel Water–Soluble . . . Alcohols", Pharmaceutical Research, vol. 10:9, 1993, pp. 1350–1355.

M. Sato et al., "Echistatin is a Potent Inhibitor of Bone Resorption in Culture", J. Cell Biology, vol. 111, 1990, pp. 1713–1723.

M. G. Saulnier et al., "An Efficient Method for the Synthesis of Guanidino Prodrugs", Bioorganic & Medicinal Chemistry Letters, vol. 4:16, 1994, pp. 1985–1990.

H. A. Staab, Syntheses Using Heterocyclic Amides (Azolides), Angew. Chem. Internat. Edit., vol. 1:7, 1962, pp. 351–367.

C. M. Storgard et al., "Decreased angiogensis and arthritic disease in rabbits treated with an $\alpha_v\beta_3$ antagonists" J. Clinical Investigation, vol. 103:1, 1999, pp. 47–54.

M. L. Stracke et al., "Tumor Cell Motility and Invasion", Encyclopedia of Cancer, vol. III, 1997, pp. 1855–1867.

M. Yamamoto et al., "The Integrin Ligand Echistatin Prevents Bone Loss in Ovariectomized Mice and Rats", Endocrinology, vol. 139:3, 1998, pp. 1411–1419.

Tian–Li Yue et al., "SK&F107260, a Cyclic RGD Peptide, Inhibits Integrin . . . Rat Carotid Artery, in vivo", Pharm. Reviews and Communications, vol. 10, 1998, pp. 9–18.

GUANIDINE DERIVATIVES AS INHIBITORS OF CELL ADHESION

BACKGROUND OF THE INVENTION

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption. Osteoporosis is a disease characterized by low bone mass and enhanced bone fragility resulting in an increased risk of fractures. It results from a deficit in new bone formation versus bone resorption during the ongoing remodelling process. Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 31 (1996) 211).

Activated osteoclasts are polynuclear cells having a diameter of up to 400 μm, which remove bone matrix. Activated osteoclasts become attached to the surface of the bone matrix and secrete proteolytic enzymes and acids into the so-called "sealing zone", the region between their cell membrane and the bone matrix. The acidic environment and the proteases cause the destruction of the bone. The compounds of the formula I inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_v\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin which contain the tripeptide motif Arg-Gly-Asp (or RGD).

Horton and coworkers describe RGD peptides and an anti-vitronectin receptor antibody (23C6) which inhibit tooth destruction by osteoclasts and the migration of osteoclasts (Horton et al., Exp. Cell. Res. 195 (1991) 368). In J. Cell Biol. 111 (1990) 1713, Sato et al. describe echistatin, an RGD peptide from snake venom, as a potent inhibitor of bone resorption in a tissue culture and as an inhibitor of osteoclast adhesion to the bones. Fisher et al. (Endocrinology 132 (1993) 1411) and Yamamoto et al. (Endocrinology 139 (1998) 1411) were able to show in the rat that echistatin also inhibits bone resorption in vivo.

It was furthermore shown that the vitronectin $\alpha_v\beta_3$ on human cells of the vascular smooth musculature of the aorta stimulates the migration of these cells into the neointima which finally leads to arteriosclerosis and restenosis after angioplasty (Brown et al., Cardiovascular Res. 28 (1994) 1815). Yue et al. (Pharmacology Reviews and Communications 10 (1998) 9) show the inhibition of neointima formation using an $\alpha_v\beta_3$ antagonist.

Brooks et al. (Cell 79 (1994) 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 31 (96) 191). The melanoma invasiveness correlated with this overexpression (Stracke et al., Encyclopedia of Cancer, volume III, p. 1855, Academic Press (1997); Hillis et al., Clinical Science 91 (1996) 639). Carron et al. (Cancer Res. 58 (1998) 1930) describe the inhibition of tumor growth and the inhibition of hypercalcemia of malignancy using an $\alpha_v\beta_3$ antagonist.

Friedlander et al. (Science 270 (1995) 1500) describe anti-$\alpha_v\beta_3$ antibodies or $\alpha_v\beta_3$ antagonists which inhibit the bFGF-induced angiogenesis processes in the rat eye, a property which can be used therapeutically in the treatment of retinopathies. Storgard et al. (J. Clin. Invest. 103 (1999) 47) describe the use of $\alpha_v\beta_3$ antagonists in the treatment of arthritic diseases.

Influencing of the vitronectin receptor or of the interactions in which it is involved thus offers the possibility of influencing different disease states for whose therapy and prophylaxis there continues to be a need for suitable pharmaceutical active ingredients.

WO-A-94/12181 describes substituted aromatic or non-aromatic ring systems, and WO-A-94/08577 describes substituted heterocycles as fibrinogen receptor antagonists and inhibitors of platelet aggregation. EP-A-528586 and EP-A-528587 disclose aminoalkyl-substituted or heterocyclyl-substituted phenylalanine derivatives, and WO-A-95/32710 discloses aryl derivatives as inhibitors of bone resorption by osteoclasts. WO-A-96/00574 describes benzodiazepines, and WO-A-96/00730 describes fibrinogen receptor antagonist templates, in particular benzodiazepines which are linked to a nitrogen-bearing 5-membered ring, as vitronectin receptor antagonists. EP-A-820991 describes cycloalkyl derivatives, WO-A-99/32457 (International Patent Application PCT/EP98/08051) describes carbamic ester derivatives, and WO-A-99/37621 (International Patent Application PCT/EP99/00242) describes sulfonamides which are vitronectin receptor antagonists. WO-A-97/06791 discloses tyrosine derived guanidino compounds as inhibitors of angiogenesis. WO-A-97/23451 discloses tyrosine derived guanidino compounds as vitronectin receptor antagonists. WO-A-98/00395 discloses phenylalanine derived acylguanidines which act both as inhibitors of the vitronectin receptor $\alpha_v\beta_3$ and of the fibrinogen receptor GP IIb/IIIa (glycoprotein IIb/IIIa). Surprisingly it was found that the acylguanidines of the formula I are particularly selective and strong inhibitors of the vitronectin receptor and of bone resorption by osteoclasts.

SUMMARY OF THE INVENTION

The present invention relates to acylguanidine derivatives of the formula I

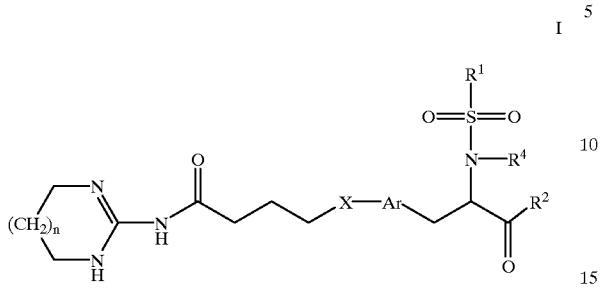

in which $R^1$, $R^2$, $R^4$, Ar, X and n have the meanings indicated below, their physiologically tolerable salts and their prodrugs. The compounds of the formula I are valuable pharmacologically active compounds. They are vitronectin receptor antagonists and inhibitors of cell adhesion. They inhibit, for example, bone resorption by osteoclasts and are suitable for the therapy and prophylaxis of diseases which are caused at least partially by an undesired extent of bone resorption, for example osteoporosis. The invention furthermore relates to processes for the preparation of compounds of the formula I, their use, in particular as active ingredients in pharmaceutical preparations, and pharmaceutical preparations comprising them.

DETAILED DESCRIPTION OF THE INVENTION

The present invention relates to compounds of the formula I

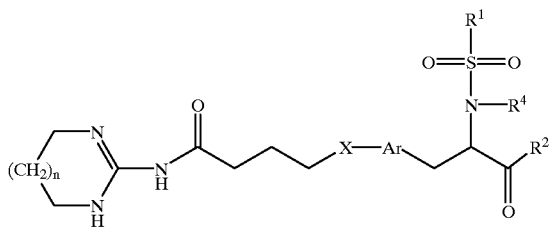

in which
$R^1$ is $(C_1-C_{20})$-alkyl, $(C_3-C_{16})$-cycloalkyl, $(C_3-C_{16})$-cycloalkyl-$(C_1-C_6)$-alkyl-, $(C_6-C_{14})$-aryl, $(C_6-C_{14})$-aryl-$(C_1-C_6)$-alkyl-, $(C_5-C_{14})$-heteroaryl or $(C_5-C_{14})$-heteroaryl-$(C_1-C_6)$-alkyl, where the alkyl residue, the cycloalkyl residue, the aryl residue and the heteroaryl residue each is unsubstituted or is substituted by one, two or three identical or different residues $R^3$, and where in the alkyl residue and the cycloalkyl residue one, two or three $CH_2$ groups can be replaced by identical or different groups selected from the series consisting of O, S and $NR^4$;

$R^2$ is hydroxy, amino, $(C_1-C_6)$-alkoxy, $(C_1-C_6)$-alkyl-CO—O—$(C_1-C_4)$-alkoxy-, $(C_3-C_{16})$-cycloalkyloxy, $(C_3-C_{16})$-cycloalkyl-CO—O—$(C_1-C_4)$-alkoxy- or $(C_6-C_{14})$-aryl-CO—O—$(C_1-C_4)$-alkoxy-, where the alkoxy residue, the alkyl residue, the aryl residue and the cycloalkyl residue each is unsubstituted or is substituted by one, two or three identical or different residues from the group consisting of hydroxy, halogen, oxo, CN, $(C_1-C_4)$-alkyl-CO—, $(C_1-C_4)$-alkyl-CO—NH—, $H_2N$—CO—, $(C_1-C_4)$-alkyl-NH—CO—, COOH, —CO—O—$(C_1-C_4)$-alkyl, $(C_1-C_4)$-alkyl, $(C_1-C_4)$-alkoxy, $(C_1-C_4)$-alkyl-S(O)$_2$—, —$NR^7R^{7'}$ and —$N^+R^7R^{7'}R^{7''}$ $Q^-$, where $R^7$, $R^{7'}$ and $R^{7''}$ independently of one another are hydrogen, $(C_1-C_6)$-alkyl, $(C_5-C_{14})$-aryl or $(C_5-C_{14})$-aryl-$(C_1-C_6)$-alkyl- and and $Q^-$ is a physiologically tolerable anion, or $R^2$ is an amino acid residue which is bonded to the CO group carrying the group $R^2$ through an amino group;

$R^3$ is $(C_1-C_8)$-alkyl, $(C_3-C_{12})$-cycloalkyl, $(C_1-C_8)$-alkoxy, $(C_6-C_{14})$-aryl, $(C_6-C_{14})$-aryl-$(C_1-C_4)$-alkyl-, halogen, trifluoromethyl, cyano, hydroxy, oxo, nitro, amino, $(C_1-C_4)$-alkyl-S(O)$_2$—, —NH—$(C_1-C_4)$-alkyl, —N(($C_1-C_4$)-alkyl)$_2$, —NH—CO—$(C_1-C_4)$-alkyl, —CO—$(C_1-C_4)$-alkyl, —CO—$NH_2$, —CO—NH—$(C_1-C_4)$-alkyl, —COOH or —CO—O—$(C_1-C_4)$-alkyl;

$R_4$ is hydrogen or $(C_1-C_8)$-alkyl;

Ar is a 6-membered monocyclic aromatic ring system containing 0, 1, 2, 3, or 4 ring nitrogen atoms which is unsubstituted or substituted with one or more identical or different residues $R^3$;

X is $CH_2$, O, $NR^4$ or S;

n is zero, one or two;

in all their stereoisomeric forms and mixtures thereof in all ratios, and their physiologically tolerable salts and their prodrugs.

All residues which can occur several times in the compounds of the formula I, for example the residues $R^3$ or $R^4$, can each independently of one another have the meanings indicated in their definitions, and can in each case be identical or different.

Alkyl residues can be straight-chain or branched and can be saturated or mono-unsaturated or poly-unsaturated. This also applies if they carry substituents or occur as substituents on other residues, for example in alkoxy residues, alkoxycarbonyl residues or arylalkyl residues. Substituted alkyl residues can be substituted in any suitable position. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, isopentyl, neopentyl, isohexyl, isodecyl, 3-methylpentyl, 2,3,4-trimethylhexyl, sec-butyl, tert-butyl, or tert-pentyl. A preferred group of alkyl residues is formed by the residues methyl, ethyl, n-propyl, isopropyl, n-butyl, isobutyl, sec-butyl and tert-butyl.

Unsaturated alkyl residues are, for example, alkenyl residues such as vinyl, 1-propenyl, allyl, butenyl or 3-methyl-2-butenyl, or alkynyl residues such as ethynyl, 1-propynyl or propargyl. Alkyl residues can also be unsaturated when they are substituted.

Cycloalkyl residues can be monocyclic, bicyclic or tricyclic, i. e., they can be monocycloalkyl residues, bicycloalkyl residues and tricycloalkyl residues, provided they have a suitable number of carbon atoms and the parent hydrocarbons are stable. A bicylic or tricyclic cycloalkyl residue has to have at least 4 carbon atoms. Preferably a bicyclic or tricyclic cycloalkyl residue has at least 5 carbon atoms, more preferably at least 6 carbon atoms, and up to the number of carbon atoms specified in the respective definition. Thus, $(C_3-C_{16})$-cycloalkyl preferably comprises but is not limited to, for example, $(C_3-C_{16})$-monocycloalkyl, ($C_6$–$C_{16}$)-bicycloalkyl and ($C_6$–$C_{16}$)-tricycloalky, and ($C_3$–$C_{12}$)-cycloalkyl preferably comprises but is not limited to, for example, ($C_3$–$C_{12}$)-monocycloalkyl, ($C_6$–$C_{12}$)-bicycloalkyl and ($C_6$–$C_{12}$)-tricycloalkyl.

Monocycloalkyl residues are, for example, cyclopropyl, cyclobutyl, cyclopentyl, cyclohexyl, cycloheptyl, cyclooctyl, cyclononyl, cyclodecyl, cycloundecyl, cyclododecyl, cyclotetradecyl or cyclohexadecyl which, can also be substituted by ($C_1$–$C_4$)-alkyl, for example. Examples of substituted cycloalkyl residues which may be mentioned are 4-methylcyclohexyl and 2,3-dimethylcyclopentyl.

Bicycloalkyl residues and tricycloalkyl residues can likewise be unsubstituted or substituted in any desired suitable position, for example by one or more oxo groups and/or one or more identical or different ($C_1$–$C_4$)-alkyl groups, for example methyl or isopropyl groups, preferably methyl groups. The free bond via which the bicyclic or the tricyclic residue is bonded can be located in any desired position in the molecule, the residue can thus be bonded via a bridgehead atom or an atom in a bridge. The free bond can also be located in any desired stereochemical position, for example in an exo-position or an endo-position. Examples of bicycloalkyl residues and tricycloalkyl residues are, camphanyl, bornyl, adamantyl such as 1-adamantyl and 2-adamantyl, caranyl, epiisobornyl, epibornyl, norbornyl and norpinanyl.

Halogen is, for example, fluorine, chlorine, bromine or iodine.

($C_5$–$C_{14}$)-Aryl includes carbocyclic ($C_6$–$C_{14}$)-aryl residues and heterocyclic ($C_5$–$C_{14}$)-aryl residues (=($C_5$–$C_{14}$)-heteroaryl residues) in which one or more of the 5 to 14 ring carbon atoms are replaced by heteroatoms such as nitrogen, oxygen or sulfur. Examples of carbocyclic ($C_6$–$C_{14}$)-aryl residues are phenyl, naphthyl, biphenylyl, anthryl or fluorenyl, where ($C_6$–$C_{12}$)-aryl residues, in particular 1-naphthyl, 2-naphthyl and phenyl, are preferred. If not stated otherwise, aryl residues, in particular phenyl residues, can be unsubstituted or substituted by one or more, preferably one, two or three, identical or different substituents. In particular substituted aryl residues can be substituted by identical or different residues from the group consisting of ($C_1$–$C_8$)-alkyl, in particular ($C_1$–$C_4$)-alkyl, ($C_1$–$C_8$)-alkoxy, in particular ($C_1$–$C_4$)-alkoxy, halogen, such as fluorine, chlorine and bromine, nitro, amino, ($C_1$–$C_4$)-alkylamino, di-(($C_1$–$C_4$)-alkyl)amino, trifluoromethyl, hydroxy, methylenedioxy, cyano, hydroxycarbonyl, aminocarbonyl, ($C_1$–$C_4$)-alkoxycarbonyl, phenyl, phenoxy, benzyl and benzyloxy. Generally, only up to two nitro groups can occur as substituents in the compounds of the formula I according to the invention.

In monosubstituted phenyl residues, the substituent can be located in the 2-position, the 3-position or the 4-position, the 3- and the 4-position being preferred. If phenyl is disubstituted, the substituents can be in the 2,3-position, 2,4-position, 2,5-position, 2,6-position, 3,4-position or 3,5-position. Preferably, in disubstituted phenyl residues, the two substituents are arranged in the 3,4-position, relative to the linkage site. In trisubstituted phenyl residues, the substituents can be in the 2,3,4-position, 2,3,5-position, 2,3,6-position, 2,4,5-position, 2,4,6-position or 3,4,5-position. Similarly, naphthyl residues and other aryl residues can be substituted in any desired position, for example a 1-naphthyl residue in the 2-, 3-, 4-, 5-, 6-, 7- and 8-position, a 2-naphthyl residue in the 1-, 3-, 4-, 5-, 6-, 7- and 8-position.

Beside carbocyclic systems, ($C_5$–$C_{14}$)-aryl groups can also be monocyclic or polycyclic, for example bicyclic or tricyclic, aromatic ring systems in which 1, 2, 3, 4 or 5 ring carbon atoms are replaced by heteroatoms, in particular by identical or different heteroatoms from the group consisting of nitrogen, oxygen and sulfur. Examples of heterocyclic ($C_5$–$C_{14}$)-aryl groups and ($C_5$–$C_{14}$)-heteroaryl groups are pyridyl like 2-pyridyl, 3-pyridyl and 4-pyridyl, pyrrolyl like 2-pyrrolyl and 3-pyrrolyl, furyl like 2-furyl and 3-furyl, thienyl like 2-thienyl and 3-thienyl, imidazolyl, pyrazolyl, oxazolyl, isoxazolyl, thiazolyl, isothiazolyl, tetrazolyl, pyridazinyl, pyrazinyl, pyrimidinyl, indolyl, isoindolyl, indazolyl, phthalazinyl, quinolinyl, isoquinolinyl, quinoxalinyl, quinazolinyl, cinnolinyl, β-carbolinyl, or benzo-fused, cyclopenta-fused, cyclohexa-fused or cyclohepta-fused derivatives of these residues. The heterocyclic systems can be substituted in all suitable positions by the same substituents as the above-mentioned carbocyclic aryl systems.

In the series of these heteroaryl groups, monocyclic or bicyclic aromatic ring systems are preferred which contain 1, 2 or 3 ring heteroatoms, in particular 1 or 2 ring heteroatoms, from the group consisting of N, O and S, and which are unsubstituted or substituted by 1, 2 or 3 substituents from the group consisting of ($C_1$–$C_6$)-alkyl, ($C_1$–$C_6$)-alkoxy, fluorine, chlorine, nitro, amino, trifluoromethyl, hydroxy, ($C_1$–$C_4$)-alkoxycarbonyl, phenyl, phenoxy, benzyloxy and benzyl, are preferred. Particularly preferred here are monocyclic or bicyclic aromatic 5-membered to 10-membered ring systems containing 1 to 3 ring heteroatoms, in particular containing 1 or 2 ring heteroatoms, from the group consisting of N, O and S, which are unsubstituted or substituted by 1 or 2 substituents from the group consisting of ($C_1$–$C_4$)-alkyl, ($C_1$–$C_4$)-alkoxy, phenyl, phenoxy, benzyl and benzyloxy. More particularly preferred are 5-membered or 6-membered monocyclic heteroaryl groups and 9-membered or 10-membered bicyclic heteroaryl groups containing 1 or 2, in particular 1, ring heteroatom from the group consisting of N, O and S which are unsubstituted or substituted as described before.

In the divalent aromatic residue —Ar— the bonds via which the group Ar is connected to the neighbouring groups can be in any desired positions. If Ar is derived from a benzene ring the residue —Ar— can be 1,2-phenylene, 1,3-phenylene or 1,4-phenylene, the latter two residues being preferred and 1,4-phenylene being especially preferred. If —Ar— is derived from a pyridine ring the two bonds via which Ar is connected can be in 1,2-position, 1,3-position or 1,4-position with respect to each other and in any desired position with respect to the ring nitrogen atom. Thus, a pyridinediyl residue representing —Ar— can be, for example, 2,3-pyridinediyl, 2,4-pyridinediyl, 2,5-pyridinediyl, 2,6-pyridinediyl, 3,4-pyridinediyl or 3,5-pyridinediyl. Preferably the two bonds via which a pyridinediyl residue representing —Ar— is connected are in 1,3-position or 1,4-position with respect to each other. An especially preferred pyridinediyl residue representing Ar is 2,5-pyridinediyl. These explanations correspondingly apply to divalent residues representing —Ar— which are derived from heterocyclic rings containing 2, 3 or 4 nitrogen atoms in the ring, i. e. to residues like pyridazinediyl, pyrimidinediyl, pyrazinediyl, 1,2,3-triazinediyl, 1,2,4-triazinediyl, 1,3,5-triazinediyl, or 1,2,4,5-tetrazinediyl.

The residue of an amino acid representing $R^2$ is obtained from the corresponding amino acid as customary in peptide chemistry by formally removing a hydrogen atom from an amino group. This amino group is then linked in peptide fashion through an amide bond to the CO group in the group $R^2$—CO in formula I. The amino acid from which $R^2$ can be derived can be a natural or unnatural amino acid and can be present in all stereochemical forms, for example in the D form, the L form or in the form of a mixture of stereoisomers, for example in the form of a racemate. Preferred amino acids are α-amino acids and β-amino acids, α-amino acids being particularly preferred. Suitable amino acids which may be mentioned include, but are not limited to, Ala, β-Ala, Arg, Asn, Asp, Cit, Cys, (Cys)$_2$, Gln, Glu, Gly, His, Ile, Leu, Lys, Met, Phe, Phg, Pro, Ser, Thr, Trp, Tyr or Val (cf. Houben-Weyl, Methoden der organischen Chemie [Methods of Organic Chemistry], Volume 15/1 and 15/2, Georg Thieme Verlag, Stuttgart (1974)). Functional groups in amino acids can be present in protected form or can be derivatized. For example, a carboxylic acid group present in an amino acid can also be present in the form of an ester or amide such as, for example, methyl ester, ethyl ester, n-propyl ester, isopropyl ester, isobutyl ester, tert-butyl ester, benzyl ester, unsubstituted amide, methylamide or ethylamide. Preferred amino acids from which an amino acid residue representing $R^2$ is derived are natural acids.

Examples of the mono-unsaturated 1,3-diazaheterocycle which is formed by the polymethylene chain —CH$_2$—(CH$_2$)$_n$—CH$_2$— in formula I together with the two endocyclic nitrogen atoms of the guanidino and the central carbon atom of the guanidino group to which these two nitrogen atoms are bonded, are the 4,5-dihydroimidazol-2-yl residue, the 1,4,5,6-tetrahydropyrimidin-2-yl residue and the 4,5,6,7-tetrahydro-1H-1,3-diazepin-2-yl residue.

Optically active carbon atoms present in the compounds of the formula I can independently of one another have R configuration or S configuration. The compounds of the formula I can be present in the form of pure enantiomers or pure diastereomers or in the form of mixtures of enantiomers, for example in the form of racemates, or of mixtures of diastereomers. The present invention relates to both pure enantiomers and mixtures of enantiomers as well as to pure diastereomers and mixtures of diastereomers. The invention comprises mixtures of two or of more than two stereoisomers of the formula I and all ratios of the stereoisomers in the mixtures. With respect to compounds of the formula I which can be present as E isomers or Z isomers, the invention relates to both pure E isomers and pure Z isomers as well as E/Z mixtures in all ratios. The invention also comprises all tautomeric forms of the compounds of the formula I, for example, beside the form shown in the formula I also the form in which the acylguanidine unit is present as a —CO—N=C(NH—CH$_2$——)—NH—CH$_2$— group, and all other forms which differ in positions of mobile hydrogen atoms. Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically unifom compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example carboxy (COOH), are for example alkali metal salts or alkaline earth metal salts such as, for example, sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine. Basic groups in the compounds of the formula I can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which simultaneously contain a basic group and an acidic group, for example the guanidino group and a carboxy group, can be present as zwitterions (betaines) which are likewise included by the present invention.

The physiologically tolerable anion $Q^-$ which is contained in the compounds of the formula I in case $R^2$ contains a positively charged ammonium group is, in particular, a monovalent anion or an eqivalent of a polyvalent anion of a nontoxic physiologically acceptable, in particular also pharmaceutically utilizable, inorganic or organic acid, for example the anion or an anion equivalent of one of the abovementioned acids suitable for the formation of acid addition salts. $Q^{31}$ can thus be, for example, one of the anions (or an anion equivalent) from the group comprising chloride, sulfate, phosphate, acetate, citrate, benzoate, maleate, fumarate, tartrate, methanesulfonate and p-toluenesulfonate.

Salts of compounds of the formula I can be obtained by customary methods known to those skilled in the art, for example by combining a compound of the formula I with an inorganic or organic acid or base in a solvent or diluent, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention moreover includes all solvates and addition compounds of the compounds of the formula I, for example hydrates or adducts with alcohols, and also derivatives of the compounds of the formula I, for example esters, prodrugs and other physiologically tolerable derivatives, as well as active metabolites of the compounds of the formula I. The invention relates in particular to prodrugs of the compounds of the formula I which can be converted into compounds of the formula I under physiological conditions. Suitable prodrugs of the compounds of the formula I, i. e. chemically modified derivatives of the compounds of the formula I having properties which are improved in a certain desired manner, are known to those skilled in the art. More detailed information relating to prodrugs is found, for example, in Fleisher et al., Advanced Drug Delivery Reviews 19 (1996) 115–130; Design of Prodrugs, H. Bundgaard (ed.), Elsevier (1985); H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350 which are all incorporated herein by reference. Suitable prodrugs of the compounds of the formula I are especially ester prodrugs and amide prodrugs of carboxylic acid groups, in particular of the COOH group which is present when $R^2$ is hydroxy, for example alkyl esters, and also acyl prodrugs and carbamate prodrugs of acylatable nitrogen-containing groups such as amino groups and in particular the guanidino group. In the acyl prodrugs or carbamate prodrugs, one or more, for example one or two, hydrogen atoms located on nitrogen atoms in such groups are replaced by an acyl group or a carbamate group. Suitable acyl groups and carbamate groups for the acyl prodrugs and carbamate prodrugs are, for example, the groups $R^{10}$—CO and $R^{11}$O—CO in which $R^{10}$ is hydrogen, $(C_1-C_{18})$-alkyl, $(C_3-C_{16})$-cycloalkyl, $(C_3-C_{16})$-cycloalkyl-$(C_1-C_8)$-alkyl-, $(C_5-C_{14})$-aryl, in which 1 to 5 carbon atoms can be replaced by heteroatoms such as N, O or S, or $(C_5-C_{14})$-aryl-$(C_1-C_8)$-alkyl-, in which 1 to 5 carbon atoms in the aryl moiety can be replaced by heteroatoms such as N, O or S, and in which $R^{11}$ has the meanings indicated for $R^{10}$ with the exception of hydrogen.

$R^1$ preferably is $(C_1-C_{10})$-alkyl, $(C_3-C_{12})$-cycloalkyl, $(C_3-C_{12})$-cycloalkyl-$(C_1-C_6)$-alkyl-, $(C_6-C_{14})$-aryl, $(C_6-C_{14})$-aryl-$(C_1-C_6)$-alkyl-, $(C_5-C_{14})$-heteroaryl or $(C_5-C_{14})$-heteroaryl-$(C_1-C_6)$-alkyl-, where the alkyl residue, the cycloalkyl residue, the aryl residue and the heteroaryl residue each is unsubstituted or is substituted by one, two or three identical or different residues $R^3$, and where in the alkyl residue and the cycloalkyl residue one, two or three $CH_2$ groups can be replaced by identical or different groups selected from the series consisting of O, S and $NR^4$. Particularly preferably $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one, two or three identical or different residues $R^3$. Very particularly preferably $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one or two identical or different residues $R^3$.

$R^2$ preferably is hydroxy, amino, $(C_1-C_6)$-alkoxy or $(C_1-C_6)$-alkyl-CO—O—$(C_1-C_4)$-alkoxy-, where the alkoxy residue and the alkyl residue each is unsubstituted or is substituted by one, two or three identical or different residues from the group consisting of hydroxy and halogen. Particularly preferably $R^2$ is hydroxy or $(C_1-C_6)$-alkoxy, where the alkoxy residue is unsubstituted or is substituted by one, two or three identical or different residues from the group consisting of hydroxy and halogen. Very particularly preferably $R^2$ is hydroxy or unsubstituted $(C_1-C_6)$-alkoxy.

$R^3$ preferably is $(C_1-C_6)$-alkyl, $(C_3-C_{12})$-cycloalkyl, $(C_1-C_6)$-alkoxy, $(C_6-C_{14})$-aryl, $(C_6-C_{14})$-aryl-$(C_1-C_4)$-alkyl-, halogen or trifluoromethyl. Particularly preferably $R^3$ is $(C_1-C_4)$-alkyl, $(C_3-C_{12})$-cycloalkyl, $(C_1-C_4)$-alkoxy, $(C_6-C_{14})$-aryl, $(C_6-C_{14})$-aryl-$(C_1-C_4)$-alkyl-, halogen or trifluoromethyl. Very particularly preferably $R^3$ is $(C_1-C_4)$-alkyl, $(C_1-C_4)$-alkoxy, $(C_6-C_{14})$-aryl, $(C_6-C_{14})$-aryl-$(C_1-C_4)$-alkyl-, halogen or trifluoromethyl.

$R^4$ preferably is hydrogen.

The residue —Ar— is preferably derived from a benzene ring or a pyridine ring, particularly preferably from a benzene ring. The two bonds via which Ar is connected to the neighbouring groups preferably are in 1,4-position with respect to each other. In case Ar is substituted it is preferably substituted by one or two identical or different residues $R^3$. Residues $R^3$ which are present as substituents on the group Ar preferably are halogen, for example fluorine, $(C_1-C_4)$-alkyl, for example methyl, or $(C_1-C_4)$-alkoxy, for example methoxy. Preferably Ar is unsubstituted. An especially preferred residue —Ar— is the unsubstituted 1,4-phenylene residue, i. e. a preferred group of compounds of the formula I are the compounds of the formula Ia.

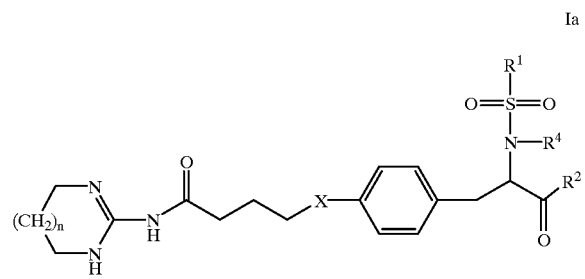

X preferably is $CH_2$ or O, particularly preferably O.

n preferably is zero or one, particularly preferably one.

Preferred compounds of the formula I are those compounds in which one or more of the residues have preferred denotations or have one or more specific denotations out of the denotations given in their respective definitions and in the general explanations on residues, all combinations of such preferred meanings and specific denotations being a subject of the present invention. Particularly preferred compounds of the formula I are those compounds in which $R^1$ is $(C_1-C_{10})$-alkyl, $(C_3-C_{12})$-cycloalkyl, $(C_3-C_{12})$-cycloalkyl-$(C_1-C_6)$-alkyl-, $(C_6-C_{14})$-aryl, $(C_6-C_{14})$-aryl-$(C_1-C_6)$-alkyl-, $(C_5-C_{14})$-heteroaryl or $(C_5-C_{14})$-heteroaryl-$(C_1-C_6)$-alkyl-, where the alkyl residue, the cycloalkyl residue, the aryl residue and the heteroaryl residue each is unsubstituted or is substituted by one, two or three identical or different residues $R^3$, and where in the alkyl residue and the cycloalkyl residue one, two or three $CH_2$ groups can be replaced by identical or different groups selected from the series consisting of O, S and $NR^4$;

$R^2$ is hydroxy, amino, $(C_1-C_6)$-alkoxy or $(C_1-C_6)$-alkyl-CO—O—$(C_114\,C_4)$-alkoxy-, where the alkoxy residue and the alkyl residue each is unsubstituted or is substituted by one, two or three identical or different residues from the group consisting of hydroxy and halogen;

$R^3$ is $(C_1-C_6)$-alkyl, $(C_3-C_{12})$-cycloalkyl, $(C_1-C_6)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is $CH_2$ or O;

n is one;

in all their stereoisomeric forms and mixtures thereof in all ratios, and their physiologically tolerable salts and their prodrugs.

Very particularly preferred compounds of the formula I are those compounds in which $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one, two or three identical or different residues $R^3$;

$R^2$ is hydroxy or $(C_1-C_6)$-alkoxy, where the alkoxy residue is unsubstituted or is substituted by one, two or three identical or different residues from the group consisting of hydroxy and halogen;

$R^3$ is $(C_1-C_4)$-alkyl, $(C_3-C_{12})$-cycloalkyl, $(C_1-C_4)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is $CH_2$ or O;

n is one;

in all their stereoisomeric forms and mixtures thereof in all ratios, and their physiologically tolerable salts and their prodrugs.

Especially preferred compounds of the formula I are those compounds in which $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one or two identical or different residues $R^3$;

$R^2$ is hydroxy or $(C_1-C_6)$-alkoxy;

$R^3$ is $(C_1-C_4)$-alkyl, $(C_1-C_4)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is O;

n is one;

in all their stereoisomeric forms and mixtures thereof in all ratios, and their physiologically tolerable salts and their prodrugs.

Preferred compounds of the formula I are additionally those in which the carbon atom to which the two groups $R^2$—CO— and $R^1$—$SO_2$—$NR^4$— are bonded has S configuration, in all their stereoisomeric forms (with respect to other stereochemical centers in the molecule) and mixtures thereof in all ratios, and their physiologically tolerable salts and their prodrugs.

The present invention also relates to processes for the preparation of the compounds of the formula I. The compounds can generally be prepared, for example in the course of a convergent synthesis, by linking two or more fragments which can be derived retrosynthetically from the formula I. In the preparation of the compounds of the formula I it can generally be advantageous or necessary in the course of the synthesis to introduce functional groups which could lead to undesired reactions or side reactions in a synthesis step in the form of precursors which are later converted into the desired functional groups, or to temporarily block functional groups by a protective group strategy suited to the respective synthesis problem. Such strategies are well known to those skilled in the art (see, for example, Greene and Wuts, Protective Groups in Organic Synthesis, Wiley (1991)). As examples of precursor groups nitro groups and cyano groups may be mentioned which can later be converted by reduction, for example by catalytic hydrogenation, into amino groups and aminomethyl groups, respectively.

The compounds of the formula I can be prepared, for example, by linking in a manner known per se a carboxylic acid or carboxylic acid derivative of the formula II,

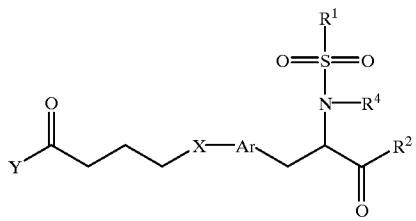

in which $R^1$, $R^2$, $R^4$, Ar and X are defined as indicated for the formula I, or in which alternatively functional groups are present in the form of precursors which are later converted into the groups present in the compounds of the formula I, or in which functional groups are present in protected form, and in which Y is a nucleophilically substitutable leaving group, with a guanidine of the formula III,

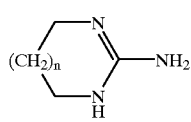

in which n is defined as indicated for the formula I.

The group COY in the formula II is preferably the carboxylic acid group COOH or an activated carboxylic acid derivative. Y can thus be, for example, hydroxy, halogen, in particular chlorine or bromine, alkoxy, in particular methoxy or ethoxy, aryloxy, for example phenoxy or pentafluorophenoxy, phenylthio, methylthio, 2-pyridylthio or a residue of a nitrogen heterocycle bonded via a nitrogen atom, in particular a residue of an azole, such as, for example, 1-imidazolyl. Y can furthermore be, for example, $((C_1-C_4)$-alkyl)—O—CO—O— or tolylsulfonyloxy and the activated acid derivative can thus be a mixed anhydride.

If Y is hydroxy, i. e. if the guanidine of the formula III is reacted with a carboxylic acid, then the carboxylic acid is expediently first activated. The activation can be carried out, for example, with carbodiimides like dicyclohexylcarbodiimide (DCCI), or with O—((cyano(ethoxycarbonyl)-methylene)amino)-1,1,3,3-tetramethyluronium tetrafluoroborate (TOTU; König et al., Proc. 21st Europ. Peptide Symp. 1990 (eds. Giralt, Andreu), Escom, Leiden (1991), p. 143), or with or 7-azabenzotriazol-1-yl-N,N,N',N'-tetramethyluronium hexafluorophosphate (HATU; L. A. Carpino, J. Am. Chem. Soc. 115 (1993) 4397), or with other activating reagents customary in peptide chemistry. A number of suitable methods for the preparation of activated carboxylic acid derivatives are also found with source literature in J. March, Advanced Organic Chemistry, Third Edition, John Wiley & Sons (1985), p. 350. The activation of the compound of the formula II in which Y is hydroxy and the reaction with the guanidine of the formula III are usually carried out in an inert solvent like, for example, tetrahydrofuran or dimethylformamide.

Beside the free guanidines of the formula III, guanidinium salts can also be employed in the reaction with the compounds of the formula II from which the free guanidines of the formula III are then prepared in situ or in a separate step by means of a base. The reaction of an activated carboxylic acid derivative of the formula II with the guanidine of the formula III is preferably carried out in a manner known per se in a protic or aprotic polar, but inert, organic solvent. For example, solvents like methanol, isopropanol, tert-butanol, dimethylformamide or tetrahydrofuran at temperatures from about 0° C. up to the boiling temperature of these solvents are suitable in the reaction of methyl esters (Y=methoxy) or of ethyl esters (Y=ethoxy) with guanidines. The reactions of compounds of the formula II with guanidines are advantageously carried out in aprotic inert solvents such as dimethylformamide, tetrahydrofuran, dimethoxyethane or dioxane, if appropriate with the addition of a base such as, for example, potassium tert-butoxide or sodium methoxide. However, water can also be used as a solvent in the reaction of compounds of the formula II with guanidines, for example when using a base such as sodium hdyroxide. If Y is, for example, chlorine the reaction is advantageously carried out with addition of an acid scavenger, for example an additional base or an excess of the guanidine of the formula III, for binding the resulting hydrohalic acid. The reaction mixture is worked up and, if desired, the reaction product is then purified by customary processes known to those skilled in the art like extraction, phase separation, destillation, crystallization, chromatography.

Protective groups which may optionally still be present in the products obtained from the compounds of the formulae II and III are then removed by standard processes. For example, a tert-butyl ester, especially a tert-butyl ester group which represents the group $COR^2$ in the formula II and which is a protected form of a COOH group representing the group $COR^2$ in the formulae I and II, can be converted into the carboxylic acid group by treatment with trifluoroacetic acid. A benzyl group can be removed by hydrogenation. A fluorenylmethoxycarbonyl group can be removed by treatment with a secondary amine. If desired, further reactions can then be carried out by standard processes, for example acylation reactions or esterification reactions. In addition, a conversion into a physiologically tolerable salt or prodrug can then be carried out by known processes.

The starting components of the formulae II and III which are linked to give the compounds of the formula I, are commercially available or can be prepared by or analogously to processes described in the literature. The preparation of starting components of the formula II which are derived from tyrosine is illustrated by way of example in Scheme 1, the present invention not being restricted to this synthesis or to these starting components. It does not cause any problems to those skilled in the art to carry out the modifications of the synthesis shown which are necessary for the preparation of other compounds according to the invention. In Scheme 1 the group Z denotes the benzyloxycarbonyl group, Et denotes ethyl and tBu denotes tert-butyl.

Scheme 1

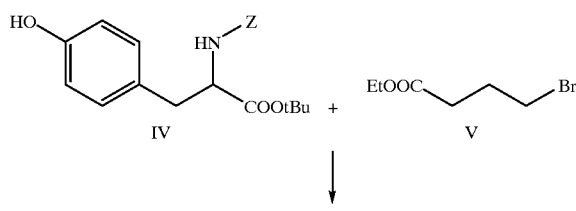

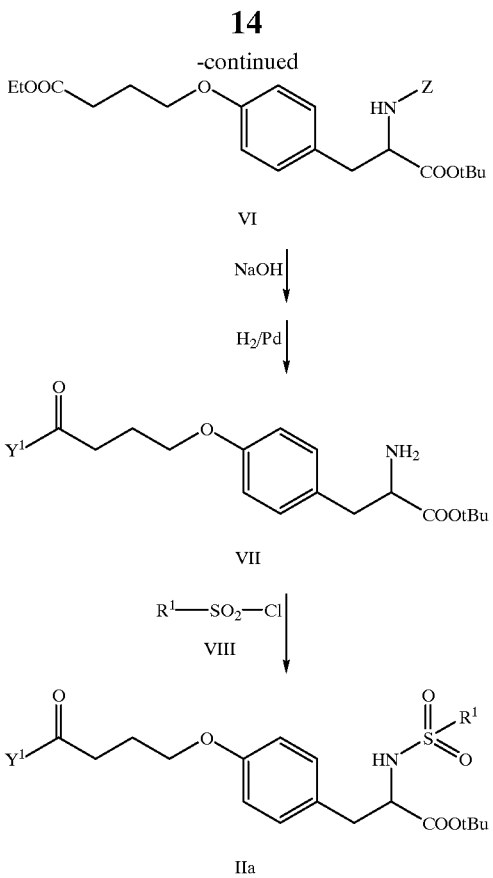

Starting materials can be tyrosine derivatives like the tyrosine tert-butyl ester of the formula IV in which the amino group is protected by the Z group. Instead of the tert-butyl ester also other esters can be employed. Alkylation with a butyric acid derivative carrying a leaving group in the 4-position like, for example, ethyl 4-bromobutyrate of the formula V leads to the compound of the formula VI. This alkylation reaction can be carried out under standard conditions for the alkylation of phenolic hydroxy groups, usually a base being added. A convenient method is, for example, refluxing the compounds of the formulae IV and V in the presence of cesium carbonate in an inert solvent like acetone (cf. WO-A-99/32457).

In the compound of the formula VI the ethyl ester group can be cleaved by standard procedures to give the carboxylic acid, for example by treatment with sodium hydroxide, and the Z group can be removed by catalytic hydrogenation under standard conditions in the presence of a catalyst like palladium on charcoal. The hydrogenation can be carried out in a solvent like, for example, an alcohol. In case that methanol is used as the solvent, depending on the reaction conditions and/or the workup procedure, an esterification leading to the methyl ester can take place. Thus, after the hydrogenation step a compound of the formula VII can be obtained in which $Y^1$ is either methoxy or hydroxy, or a mixture of compounds of the formula VII can be obtained in which $Y^1$ is methoxy and hydroxy and which can conveniently be converted into the acid or the ester by standard procedures for saponification or esterification, respectively, or which can be separated.

For the introduction of the sulfonyl group $R^1$—$SO_2$ the compound of the formula VII can then be reacted with a sulfonyl chloride of the formula VIII in which $R^1$ has the meanings indicated above for formula I, or with another suitable sulfonic acid derivative. The formation of the sulfonamide is usually carried out in the presence of a base, for example a tertiary amine like triethylamine or diisopropylethylamine, in an inert solvent, for example dimethylformamide or a chlorinated hydrocarbon like methylene chloride. The sulfonic acid chlorides of the formula VIII are commercially available or can be prepared according to or analogously to procedures described in the literature.

The resulting compounds of the formula II in which $Y^1$ is, for example, hydroxy of methoxy are examples of compounds of the formula II in which Y is hydroxy or methoxy. These compounds and analogous compounds which are obtained from a synthesis like that described above and which contain a group that is an activated carboxylic acid derivative, can be reacted directly with the compounds of the formula III. The compounds of the formula II obtained in the above synthesis in which the group $COY^1$ is an ester group, for example the group $COOCH_3$, can also first be converted by cleavage of the ester group under standard conditions into the corresponding carboxylic acids which are then reacted with the guanidines of the formula III after in situ activation, for example with HATU, TOTU or DCCI as explained above, or after conversion into an activated carboxylic acid derivative. If it is intended to prepare as activated carboxylic acid derivative, for example, the carboxylic acid chloride (formula II, Y=Cl) this conversion can be carried out by using thionyl chloride, for example. If it is intended to prepare, for example, the methyl ester (formula II, Y=methoxy) from the carboxylic acid this can be carried out by treatment with gaseous hydrogen chloride in methanol. Other activated acid derivatives can be prepared in a manner known per se from the carboxylic acid chlorides or directly from the carboxylic acids (formula II, Y=OH) on which they are based. Example of such derivatives are the imidazolides (formula II, Y=1-imidazolyl) which are obtained by treating the acids with carbonyldiimidazole (cf. Staab, Angew. Chem. Int. Ed. Engl. 1 (1962) 351–367), or the mixed anhydrides which are obtained, for example, by reaction with chloroformic acid esters such as ethyl chloroformate or with tosyl chloride in the presence of amines such as triethylamine in an inert solvent. A number of suitable methods for the preparation of activated carboxylic acid derivatives are found with source literature in J. March, Advanced Organic Chemistry, Third Edition, John Wiley & Sons (1985), p. 350.

An alkyl group representing the group $R^4$ in the group $NR^4$—$SO_2R^1$ can be introduced, for example, by monoalkylating a compound of the formula VII on the nitrogen atom under standard conditions. Such a alkylation can favorably be achieved by condensing the amino group with an aldehyde and reducing the resulting imine, for example with a complex hydride like sodium borohydride, i. e. by the method of reductive amination. The resulting compound containing a group $R^4NH$ can then be reacted with a sulfonyl chloride of the formula VIII as explained for the compounds of the formula VII. Another method for introducing an alkyl group representing the group $R^4$ in the group $NR^4$—$SO_2R^1$ is the alkylation of the sulfonamide of the formula II a on the nitrogen atom with an alkyl halogenide.

Compounds of the formula II in which X is S or $NR^4$ can be prepared analogously to the procedure described above for the compounds in which X is O. In this case a 4-mercaptophenylalanine derivative or a 4-aminophenylalanine derivative, respectively, is employed as the starting compound. Compounds of the formula II in which X is $CH_2$ can be prepared starting from 4-iodophenylalanine derivatives which are reacted with alkene carboxylic acid derivatives or alkyne carboxylic acid derivatives in a Heck reaction in the presence of a palladium catalyst under usual conditions. For example, a derivative of 4-iodophenylalanine of the formula I—$C_6H_4$—$CH_2$—CH($NH_2$)—COOH in which the amino group and the carboxylic acid group are protected is reacted with ethyl pent-4-enoate of the formula $CH_2$=CH—$CH_2$—$CH_2$—$COOC_2H_5$. In the coupling product obtained in the Heck reaction the carbon-carbon double bond or triple bond, respectively, is then converted into a single bond by catalytic hydrogenation, and the resulting intermediate compound which corresponds to a compound of the formulae VI or VII is then employed in the subsequent reaction steps described above.

The compounds of the formula I are valuable pharmacologically active compounds which are suitable, for example, for the therapy and prophylaxis of bone disorders, tumor diseases or cardiovascular disorders. The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which, as active constituent, contain an efficacious dose of at least one compound of the formula I and/or its physiologically tolerable salts and/or its prodrugs and a pharmaceutically acceptable carrier.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders, and also to the use of the compounds of the formula I and/or their physiologically tolerable salts and/or their prodrugs for the therapy and prophylaxis of these diseases and to methods for such therapy and prophylaxis. The present invention furthermore relates to pharmaceutical preparations (or pharmaceutical compositions) which contain an effective amount of at least one compound of the formula I and/or its physiologically tolerable salts and/or its prodrugs and a customary pharmaceutically acceptable carrier, i. e. one or more pharmaceutically acceptable carrier substances and/or additives.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula I and/or its (their) physiologically tolerable salts and/or its (their) prodrugs. For the production of pills, tablets, coated tablets and hard gelatin capsules, it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5 to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.2 to about 500 mg, preferably from about 1 to about 200 mg.

In addition to the active ingredients of the formula I and carrier substances, the pharmaceutical preparations can contain additives (or auxiliaries), such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and inhibitors of cell adhesion. They have, for example, the ability to inhibit the binding of osteoclasts to the bone surface and thereby inhibit bone resorption by osteoclasts. The action of the compounds of the formula I can be demonstrated, for example, in an assay in which the inhibition of the binding of the isolated vitronectin receptor or of cells which contain the vitronectin receptor to a ligand of the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compounds of the formula I and their physiologically tolerable salts and their prodrugs are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with agents like bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical preparation, for example tablets, capsules or granules, or can be present in two or more separate pharmaceutical preparations which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also subjects of the present invention. The invention furthermore relates to pharmaceutical preparations which comprise efficacious amounts of at least one compound of the formula I and/or its physiologically tolerable salts and/or its prodrugs together with at least one other active ingredient effective in the treatment or prophylaxis of osteoporosis or in the inhibition of bone resorption like those listed before, together with a customary pharmaceutically acceptable carrier. The above explanations on pharmaceutical preparations correspondingly apply to such pharmaceutical combination preparations.

Apart from use as inhibitors of bone resorption by osteoclasts, the compounds of the formula I and their physiologically tolerable salts and their prodrugs can be used, for example, as inhibitors of tumor growth and tumor metastasis, as anti-inflammatories, for the therapy or prophylaxis of cardiovascular disorders such as arteriosclerosis or restenosis, for the therapy or prophylaxis of nephropathies or retinopathies such as, for example, diabetic retinopathy, or for the therapy or prophylaxis of rheumatoid arthritis. As inhibitors of tumor growth or tumor metastasis the compounds of the formula I and/or their physiologically tolerable salts and/or their prodrugs can also favorably be used in combination with conventional cancer therapies. Examples of conventional cancer therapy are given in Bertino (Editor), Encyclopedia of Cancer, Academic Press (1997) which is incorporated herein by reference. All the above statements relating to the use of the compounds of formula I in combination with conventional osteoporosis therapy like, for example, possible modes of administration and pharmaceutical combination preparations, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed, on the nature and severity of the disease to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, for example from about 0.3 to about 0.5 mg/kg to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Apart from use as pharmaceutical active ingredients, the compounds of the formula I can also be used as vehicles or carriers for other active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag which is incorporated herein by reference). The active ingredients to be transported are in particular those which can be used for the treatment of the abovementioned diseases.

The compounds of the formula I and their salts can furthermore be employed for diagnostic purposes, for example in in vitro diagnoses, and as auxiliaries in biochemical investigations in which blocking of the vitronectin receptor or influencing of cell-cell or cell-matrix interactions is desired. They can furthermore be used as synthesis intermediates for the preparation of other compounds, in particular of other pharmaceutical active ingredients, which are obtainable from the compounds of the formula I, for example, by introduction of substituents or modification of functional groups.

EXAMPLES

Example 1

(2S)-2-(Naphthalene-2-sulfonylamino)-3-{4-[3-(1,4, 5,6-tetrahydropyrimidin-2-ylcarbamoyl)-propoxy]-phenyl}-propionic acid

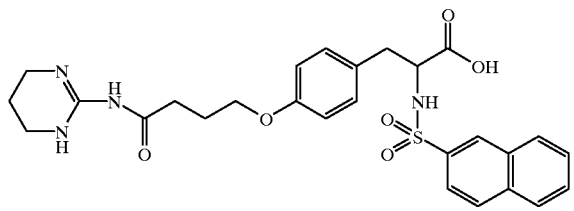

(a) 4-{4-[(2S)-2-tert-Butoxycarbonyl-2-(naphthalene-2-sulfonylamino)-ethyl]-phenoxy}-butyric acid methyl ester 250 mg of 4-[4-((2S)-2-amino-2-tert-butoxycarbonyl-ethyl)-phenoxy]-butyric acid methyl ester acetic acid salt were dissolved in dichloromethane and shaken three times with saturated aqueous sodium bicarbonate solution. The organic phase was dried with sodium sulfate, filtered and the solvent was removed in vacuo. The residue was dissolved in dichloromethane (5 ml) and treated with 142 mg of 2-naphthalenesulfonyl chloride and 0.325 ml of triethylamine. The reaction mixture was stirred for 48 hours, then diluted with dichloromethane and washed three times with water. The organic phase was dried with sodium sulfate, filtered and the solvent was removed in vacuo. The residue was chromatographed on silica gel eluting with n-heptane/ethyl acetate (2/1). Yield 155 mg. $R_f$ (n-heptane/ethyl acetate (1/1)): 0.56. MS (ES$^+$): m/e=528.2 (M+H)$^+$; 472.1.

(b) (2S)-2-(Naphthalene-2-sulfonylamino)-3-{4-[3-(1,4,5,6-tetrahydropyrimidin-2-ylcarbamoyl)-propoxy]-phenyl}-propionic acid tert-butyl ester 145 mg of 4{-4-[(2S)-2-tert-butoxycarbonyl-2-(naphthalene-2-sulfonylamino)-ethyl]-phenoxy}-butyric acid methyl ester were dissolved in 2 ml of DMF (dimethylformamide) and 134 mg of 1,4,5,6-tetrahydropyrimidin-2-ylamine were added. The reaction mixture was stirred overnight, and the solvent was removed in vacuo. The residue was chromatographed on silica gel eluting with dichloromethane, followed by dichloromethane/methanol (10/1). Yield 127 mg. $R_f$ (dichloromethane/methanol/water/acetic acid (85/15/1.5/1.5)): 0.63. MS (ES$^+$): m/e=595.2 (M+H)$^+$.

(c) (2S)-2-(Naphthalene-2-sulfonylamino)-3-{4-[3-(1,4,5,6-tetrahydropyrimidin-2-ylcarbamoyl)-propoxy]-phenyl}-propionic acid 127 mg of (2S)-2-(naphthalene-2-sulfonylamino)-3-{4-[3-(1,4,5,6-tetrahydropyrimidin-2-ylcarbamoyl-)-propoxy]-phenyl}-propionix acid tert-butyl ester were dissolved in 0.5 ml of dichloromethane and 0.5 ml of trifluoroacetic acid were added. After 3 hours the solvent was removed in vacuo, and toluene was added to the residue and then removed in vacuo. The residue was dissolved in acetonitrile/water (1/1) and lyophilized. Yield 84 mg. $R_f$ (dichloromethane/methanol/water/acetic acid (85/15/1.5/1.5)): 0.56. MS (ES$^+$): m/e=539.2 (M+H)$^+$.

Example 2

(2S)-2-(Naphthalene-1-sulfonylamino)-3-{4-[3-(1,4, 5,6-tetrahydropyrimidin-2-ylcarbamoyl)-propoxy]-phenyl}-propionic acid

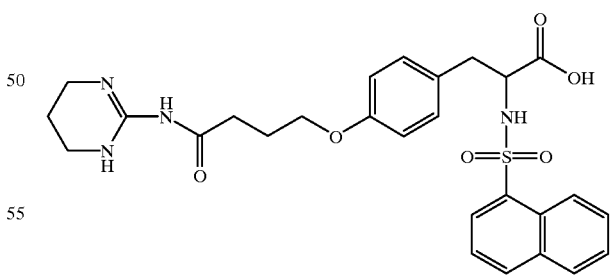

(a) 4-{4-[(2S)-2-tert-Butoxycarbonyl-2-(naphthalene-1-sulfonylamino)-ethyl]-phenoxy}-butyric acid 23.3 mg of 4-[4-[(2S)-2-amino-2-tert-butoxycarbonyl-ethyl)]-phenoxy]-butyric acid were dissolved in 2 ml of DMF and cooled to 0° C. 173 mg of 1-naphthalenesulfonyl chloride and 0.26 ml of diisopropylethylamine were added and the reaction mixture was stirred at 0° C. for 2 hours. The reaction was quenched by the addition of water, and the mixture was extracted three times with dichloromethane. The combined organic phases were dried with sodium sulfate, filtered and the solvent was removed in vacuo. The residue was chromatographed on silica gel eluting with dichloromethane/methanol/water/acetic acid (9/1/0.1/0.1). Yield 61 mg. MS (ES$^+$): m/e=514.2 (M+H)$^+$; 458.1.

(b) (2S)-2-(Naphthalene-1-sulfonylamino)-3-{4-[3-(1,4,5,6-tetrahydropyrimidin-2-ylcarbamoyl)-propoxy]-phenyl}-propionic acid tert-butyl ester 61 mg of 4-{4-[(2S)-2-tert-butoxycarbonyl-2-(naphthalene-1-sulfonylamino)-ethyl]-phenoxy}-butyric acid were dissolved in tetrahydrofuran and 14 mg of 1,4,5,6-tetrahydropyrimidin-2-ylamine, 0.103 ml of diisopropylethylamine and 49.7 mg of 7-azabenzotriazol-1-yl-N,N,N′,N′-tetramethyluronium hexafluorophosphate (HATU) were added. The reaction mixture was stirred overnight, and the solvent was removed in vacuo. The residue was dissolved in dichloromethane and washed with saturated aqueous sodium bicarbonate solution and saturated aqueous sodium chloride solution. The organic phase was dried with sodium sulfate, filtered and the solvent was removed in vacuo. The residue was chromatographed on reversed-phase (C-18) silica gel eluting with a gradient of 10–90% acetonitrile in water. Yield 31 mg. MS (FAB$^+$): m/e=595.3 (M+H)$^+$.

(c) (2S)-2-(Naphthalene-1-sulfonylamino)-3-{4-[3-(1,4,5,6-tetrahydropyrimidin-2-ylcarbamoyl)-propoxy]-phenyl}-propionic acid 31 mg of (2S)-2-(naphthalene-1-sulfonylamino)-3-{4-[3-(1,4,5,6-tetrahydropyrimidin-2-ylcarbamoyl)-propoxy]-phenyl}-propionic acid tert-butyl ester were dissolved in trifluoroacetic acid/water (95/5) and stirred for 2 hours. The solvent was removed in vacuo, and the residue was dissolved in acetic acid/water and lyophilized. Yield 19.7 mg. MS (ES$^+$): m/e=539.3 (M+H)$^+$.

Example 3

(2S)-2-(4-Chlorobenzenesulfonylamino)-3-{4-[3-(1,4,5,6-tetrahydropyrimidin-2-ylcarbamoyl)-propoxy]-phenyl}-propionic acid

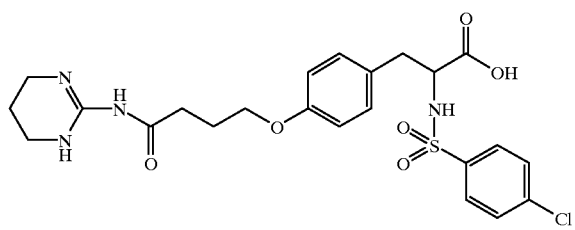

(a) 4-{4-[(2S)-2-tert-Butoxycarbonyl-2-(4-chlorobenzenesulfonylamino)-ethyl]-phenoxy}-butyric acid 200 mg of 4-[4-((2S)-2-amino-2-tert-butoxycarbonyl-ethyl)-phenoxy]-butyric acid were dissolved in 2 ml of DMF and cooled to 0° C. 220 mg of 4-chlorobenzenesulfonyl chloride and 270 mg of diisopropylethylamine were added and the reaction mixture was stirred at 0° C. for 2 hours. The reaction mixture was cooled to −25° C. for 16 hours and then warmed to room temperature. The reaction was quenched by the addition of water, and the mixture was extracted three times with dichloromethane. The combined organic phases were dried with sodium sulfate, filtered and the solvent was removed in vacuo. The residue was chromatographed on silica gel eluting with dichloromethane/methanol/water/acetic acid (9/1/0.1/0.1). Yield 84 mg. MS (ES$^+$): m/e=498.1 (M+H)$^+$; 442.1.

(b) (2S)-2-(4-Chlorobenzenesulfonylamino)-3-{4-[3-(1,4,5,6-tetrahydropyrimidin-2-ylcarbamoyl)-propoxy]-phenyl}-propionic acid tert-butyl ester 74 mg of 4-{4-(2S)-2-tert-butoxycarbonyl-2-(4-chlorobenzenesulfonylamino)-ethyl]-phenoxy}-butyric acid were dissolved in tetrahydrofuran and 23 mg of 1,4,5,6-tetrahydropyrimidin-2-ylamine, 96 mg of diisopropylethylamine and 62 mg of HATU were added. The reaction mixture was stirred overnight, and the solvent was removed in vacuo. The residue was dissolved in dichloromethane and washed with saturated aqueous sodium bicarbonate solution and saturated aqueous sodium chloride solution. The organic phase was dried with sodium sulfate, filtered and the solvent was removed in vacuo. The residue was chromatographed on reversed-phase (C-18) silica gel eluting with a gradient of 10–90% acetonitrile in water. Yield 35.7 mg. MS (FAB$^+$): m/e=579.2 (M)$^+$.

(c) (2S)-2-(4-Chlorobenzenesulfonylamino)-3-{4-[3-(1,4,5,6-tetrahydropyrimidin-2-ylcarbamoyl)-propoxy]-phenyl}-propionic acid 35.7 mg of (2S)-2-(4-chlorobenzenesulfonylamino)-3-{4-[3-(1,4,5,6-tetrahydropyrimidin-2-ylcarbamoyl)-propoxy]-phenyl}-propionic acid tert-butyl ester were dissolved in trifluoroacetic acid/water (95/5) and stirred for 2 hours. The solvent was removed in vacuo. The residue was dissolved in acetic acid/water and lyophilized. Yield 20.2 mg. MS (ES$^+$): m/e=523.1 (M)$^+$.

Example 4

(2S)-2-Benzenesulfonylamino-3-{4-[3-(1,4,5,6-tetrahydropyrimidin-2-ylcarbamoyl)-propoxy]-phenyl}-propionic acid

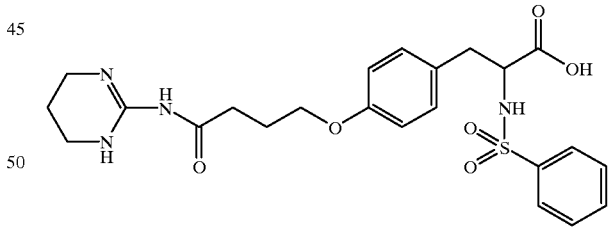

(a) 4-[4-((2S)-2-Benzenesulfonylamino-2-tert-butoxycarbonyl-ethyl)-phenoxy]-butyric acid 224.5 mg of 4-[4-((2S)-2-amino-2-tert-butoxycarbonyl-ethyl)-phenoxy]-butyric acid were dissolved in 2 ml of DMF and cooled to 0° C. 207 mg of benzenesulfonyl chloride and 303 mg of diisopropylethylamine were added and the reaction mixture was stirred at 0° C. for 2 hours. The reaction mixture was cooled to −25° C. for 16 hours and then warmed to room temperature. The reaction was quenched by the addition of water, and the mixture was extracted three times with dichloromethane. The combined organic phases were dried with sodium sulfate, filtered and the solvent was

(b) (2S)-2-Benzenesulfonylamino-3-{4-[3-(1,4,5,6-tetrahydropyrimidin-2-ylcarbamoyl)-propoxy]-phenyl}-propionic acid tert-butyl ester 88 mg of 4-[4-((2S)-2-benzenesulfonylamino-2-tert-butoxycarbonyl-ethyl)-phenoxy]-butyric acid were dissolved in tetrahydrofuran and 22.6 mg of 1,4,5,6-tetrahydropyrimidin-2-ylamine, 123 mg of diisopropylethylamine and 79.4 mg of HATU were added. The reaction mixture was stirred overnight, and the solvent was removed in vacuo. The residue was dissolved in dichloromethane and washed with saturated aqueous sodium bicarbonate solution and saturated aqueous sodium chloride solution. The organic phase was dried with sodium sulfate, filtered and the solvent was removed in vacuo. The residue was chromatographed on reversed-phase (C-18) silica gel eluting with a gradient of 10–90% acetonitrile in water. Yield 40.1 mg. MS (FAB$^+$): m/e=545.3 (M+H)$^+$.

(c) (2S)-2-Benzenesulfonylamino-3-{4-[3-(1,4,5,6-tetrahydropyrimidin-2-ylcarbamoyl)-propoxy]-phenyl}-propionic acid 40.1 mg of (2S)-2-benzenesulfonylamino-3-{4-[3-(1,4,5,6-tetrahydropyrimidin-2-ylcarbamoyl)-propoxy]-phenyl}-propionic acid tert-butyl ester were dissolved in trifluoroacetic acid/water (95/5) and stirred for 2 hours. The solvent was removed in vacuo, and the residue was dissolved in acetic acid/water and lyophilized. Yield 24 mg. MS (ES$^+$): m/e=489.2 (M+H)$^+$.

Example 5

(2S)-3-{4-[3-(1,4,5,6-Tetrahydropyrimidin-2-ylcarbamoyl)-propoxy]-phenyl}-2-(4-trifluoromethylbenzenesulfonylamino)-propionic acid

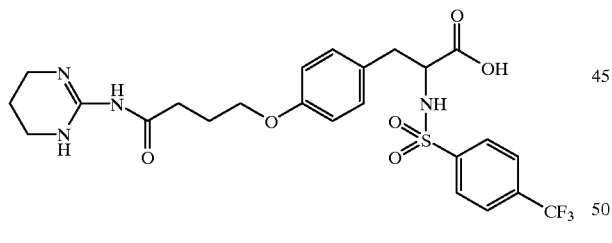

(a) 4-{4-[(2S)-2-tert-Butoxycarbonyl-2-(4-trifluoromethylbenzensulfonylamino)ethyl]-phenoxy}-butyric acid 210.5 mg of 4-[4-((2S)-2-amino-2-tert-butoxycarbonyl-ethyl)-phenoxy]-butyric acid were dissolved in 2 ml of DMF and cooled to 0° C. 269 mg of 4-trifluoromethylbenzenesulfonyl chloride and 284 mg of diisopropylethylamine were added and the reaction mixture was stirred at 0° C. for 2 hours. The reaction mixture was cooled to –25° C. for 16 hours and then warmed to room temperature. The reaction was quenched by the addition of water, and the mixture was extracted three times with dichloromethane. The combined organic phases were dried with sodium sulfate, filtered and the solvent was removed in vacuo. The residue was chromatographed on silica gel eluting with dichloromethane/methanol/water/acetic acid (9/1/0.1/0.1). Yield 98 mg. MS (ES$^+$): m/e=464.1 (M+H)$^+$; 408.1.

(b) (2S)-3-{4-[3-(1,4,5,6-Tetrahydropyrimidin-2-ylcarbamoyl)-propoxy]-phenyl}-2-(4-trifluoromethylbenzenesulfonylamino)-propionic acid tert-butyl ester 56 mg of 4-{4-[(2S)-2-tert-butoxycarbonyl-2-(4-trifluoromethylbenzenesulfonylamino)-ethyl]-phenoxy}-butyric acid were dissolved in tetrahydrofuran and 12.5 mg of 1,4,5,6-tetrahydropyrimidin-2-ylamine, 68 mg of diisopropylethylamine and 44 mg of HATU were added. The reaction mixture was stirred overnight, and the solvent was removed in vacuo. The residue was dissolved in dichloromethane and washed with saturated aqueous sodium bicarbonate solution and saturated aqueous sodium chloride solution. The organic phase was dried with sodium sulfate, filtered and the solvent was removed in vacuo. The residue was chromatographed on reversed-phase (C-18) silica gel eluting with a gradient of 10–90% acetonitrile in water. Yield 37.3 mg. MS (FAB$^+$): m/e=613.3 (M+H)$^+$.

(c) (2S)-3-{4-[3-(1,4,5,6-Tetrahydropyrimidin-2-ylcarbamoyl)-propoxy]-phenyl}-2-(4-trifluoromethylbenzenesulfonylamino)-propionic acid 37.3 mg of (2S)-3-{4-[3-(1,4,5,6-tetrahydropyrimidin-2-ylcarbamoyl)-propoxy]-phenyl}-2-(4-trifluoromethylbenzenesulfonylamino)-propionic acid tert-butyl ester were dissolved in trifluoroacetic acid/water (95/5) and stirred for 2 hours. The solvent was removed in vacuo, and the residue was dissolved in acetic acid/water and lyophilized. Yield 27.6 mg. MS (ES$^+$): m/e=557.1 (M+H)$^+$.

Example 6

(2S)-3-{4-[3-(1,4,5,6-Tetrahydropyrimidin-2-ylcarbamoyl)-propoxy]-phenyl}-2-(toluene4-sulfonylamino)-propionic acid

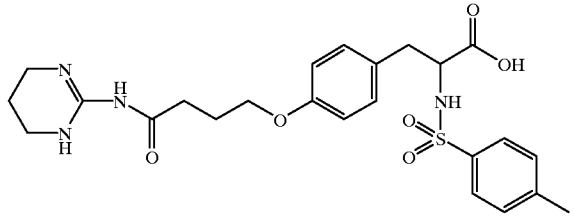

(a) 4-{4-[(2S)-2-tert-Butoxycarbonyl-2-(toluene-4-sulfonylamino)-ethyl]-phenoxy}-butyric acid ethyl ester 411 mg of 4-[4-((2S)-2-amino-2-tert-butoxycarbonyl-ethyl)-phenoxy]-butyric acid ethyl ester were dissolved in 10 ml of anhydrous DMF and cooled to 0° C. 191 mg of 4-toluenesulfonyl chloride and 0.34 ml of diisopropylethylamine were added and the reaction mixture was stirred at room temperature overnight. The reaction mixture was filtered and the solvents removed in vacuo. The residue was chromatographed on silica gel eluting with n-heptane/ethyl acetate (1/1). Yield 295 mg. MS (ES$^+$): m/e=506.2 (M+H)$^+$; 450.2.

(b) (2S)-3-{4-[3-(1,4,5,6-Tetrahydropyrimidin-2-ylcarbamoyl)-propoxy]-phenyl}-2-(toluene4-sulfonylamino)-propionic acid tert-butyl ester 295 mg of 4-{4-[(2S)-2-tert-Butoxycarbonyl-2-(toluene-4-sulfonylamino)-ethyl]-phenoxy}-butyric acid ethyl ester were dissolved in 15 ml of anhydrous DMF and 287 mg of 1,4,5,6-tetrahydropyrimidin-2-ylamine were added to the solution. The reaction mixture was stirred overnight at room temperature, and the solvent was removed in vacuo. The residue was dissolved in dichloromethane and washed with saturated aqueous sodium bicarbonate solution and saturated aqueous sodium chloride solution. The organic phase was dried with anhydrous magnesium sulfate, filtered and the solvent was removed in vacuo. The residue was chromatographed on silica gel eluting with a gradient of ethyl acetate/isopropanole/water (8/3/1 to 4/3/1). Yield 241 mg. MS: m/e=559.2 (M+H)$^+$; 503.2.

(c) (2S)-3-{4-[3-(1,4,5,6-Tetrahydropyrimidin-2-ylcarbamoyl)-propoxy]-phenyl}-2-(toluene4-sulfonylamino)-propionic acid 240 mg of (2S)-3-{4-[3-(1,4,5,6-tetrahydropyrimidin-2-ylcarbamoyl)-propoxy]-phenyl}-2-(toluene-4-sulfonylamino)-propionic acid tert-butyl ester were dissolved in 5 ml of methylene chloride and 1.6 ml of trifluoroacetic acid/water (95/5). The mixture was stirred for 2 hours at ambient temperature. The solvents were removed in vacuo. The residue was triturated with diethyl ether, filtered and dried in vacuo. Yield 196 mg. MS (ES$^+$): m/e=503.1 (M+H)$^+$.

The following examples 7 to 10 were prepared analogously to the procedure described in example 6.

Example 7

(2S)-2-(4-Bromobenzenesulfonylamino)-3-{4-[3-(1,4,5,6-tetrahydropyrimidin-2-ylcarbamoyl)-propoxy]-phenyl}-propionic acid

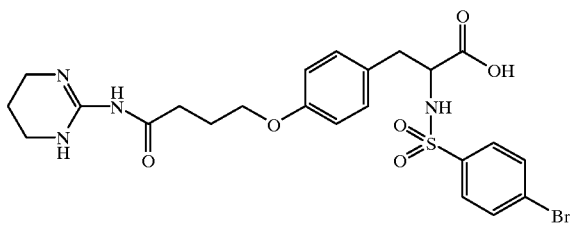

MS (ES$^+$): m/e=567.1 and 569.1 (M+H)$^+$.

Example 8

(2S)-3-{4-[3-(1,4,5,6-Tetrahydropyrimidin-2-ylcarbamoyl)-propoxy]-phenyl}-2-(thiophene-2-sulfonylamino)-propionic acid

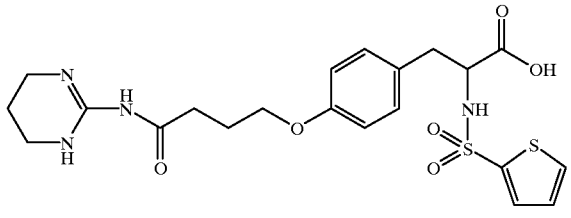

MS (ES$^+$): m/e=495.2 (M+H)$^+$.

Example 9

(2S)-2-(Butane-1-sulfonylamino)-3-{4-[3-(1,4,5,6-tetrahydropyrimidin-2-ylcarbamoyl)-propoxy]-phenyl}-propionic acid

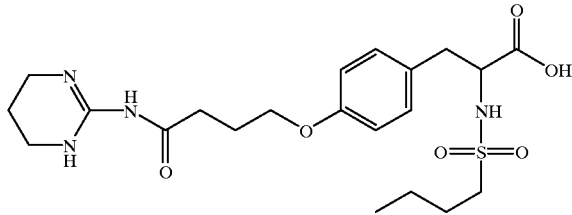

MS (ES$^+$): m/e=469.3 (M+H)$^+$.

Example 10

(2S)-2-(Octane-1-sulfonylamino)-3-{4-[3-(1,4,5,6-tetrahydropyrimidin-2-ylcarbamoyl)-propoxy]-phenyl}-propionic acid

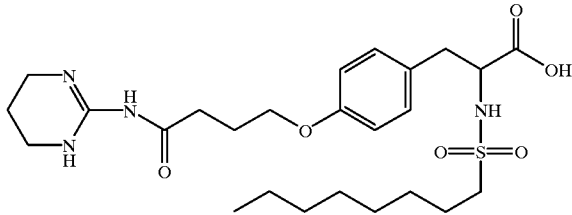

MS (ES$^+$): m/e=525.3 (M+H)$^+$.

Pharmacological Testing

The inhibition of bone resorption by the compounds according to the invention can be determined, for example, with the aid of an osteoclast resorption test ("PIT ASSAY"), for example analogously to WO-A-95/32710 which is incorporated herein by reference.

The inhibition of the binding of kistrin to human vitronectin receptor (VnR) described below is a test method by which, for example, the antagonistic action of the compounds according to the invention on the vitronectin receptor $\alpha_v\beta_3$ can be determined ($\alpha_v\beta_3$ ELISA Test; the test method is abbreviated as "K/VnR" in the listing of the test results).

Purification of Kistrin

Kistrin was purified according to the methods of Dennis et al., as described in Proc. Natl. Acad. Sci. USA 87 (1989) 2471–2475 and PROTEINS: Structure, Function and Genetics 15 (1993) 312–321.

Purification of Human Vitronectin Receptor ($\alpha_v\beta_3$)

Human vitronectin receptor was obtained from the human placenta according to the method of Pytela et al., Methods Enzymol. 144 (1987) 475. Human vitronectin receptor $\alpha_v\beta_3$ can also be obtained from some cell lines (for example from 293 cells, a human embryonic kidney cell line) which are co-transfected with DNA sequences for both subunits $\alpha_v$ and $\beta_3$ of the vitronectin receptor. The subunits are extracted with octyl glycoside and then chromatographed through concanavalin A, heparin-Sepharose and S-300.

Monoclonal Antibodies

Murine monoclonal antibodies which are specific for the $\beta_3$ subunits of the vitronectin receptor were prepared according to the method of Newman et al., Blood (1985) 227–232, or by a similar process. The rabbit Fab 2 anti-mouse Fc conjugate to horseradish peroxidase (anti-mouse Fc HRP) was obtained from Pel Freeze (Catalog No. 715 305-1).

ELISA Test

The ability of substances to inhibit the binding of kistrin to the vitronectin receptor can be determined using an ELISA test. For this purpose, Nunc 96-well microtiter plates were coated with a solution of kistrin (0.002 mg/ml) according to the method of Dennis et al., as described in PROTEINS: Structure, Function and Genetics 15 (1993) 312–321. The plates were then washed twice with PBS/0.05% Tween-20 and blocked by incubating (60 min) with bovine serum albumin (BSA, 0.5%, RIA grade or better) in buffer solution (Tris-HCl (50 mM), NaCl (100 mM), $MgCl_2$ (1 mM), $CaCl_2$ (1 mM), $MnCl_2$ (1 mM), pH 7). Solutions of known inhibitors and of the test substances were prepared in concentrations from $2\times10^{-12}$ to $2\times10^{-6}$ mol/l in assay buffer (BSA (0.5%, RIA grade or better); Tris-HCl (50 mM), NaCl (100 mM), $MgCl_2$ (1 mM), $CaCl_2$ (1 mM), $MnCl_2$ (1 mM), pH 7). The blocked plates were emptied, and in each case 0.025 ml of this solution which contained a defined concentration ($2\times10^{-12}$ to $2\times10^{-6}$ mol/l) either of a known inhibitor or of a test substance, were added to each well. 0.025 ml of a solution of the vitronectin receptor in assay buffer (0.03 mg/ml) was pipetted into each well of the plate and the plate was incubated at room temperature for 60–180 min on a shaker. In the meantime, a solution (6 ml/plate) of a murine monoclonal antibody specific for the $\beta_3$ subunit of the vitronectin receptor was prepared in assay buffer (0.0015 mg/ml). A second rabbit antibody (0.001 ml of stock solution/6 ml of the murine monoclonal anti-$\beta_3$ antibody solution) which was an anti-mouse Fc HRP antibody conjugate was added to this solution, and this mixture of murine anti-$\beta_3$ antibody and rabbit anti-mouse Fc HRP antibody conjugate was incubated during the time of the receptor-inhibitor incubation. The test plates were washed four times with PBS solution which contained 0.05% Tween-20, and in each case 0.05 ml/well of the antibody mixture was pipetted into each well of the plate and incubated for 60–180 min. The plate was washed four times with PBS/0.05% Tween-20 and then developed with 0.05 ml/well of a PBS solution which contained 0.67 mg/ml of o-phenylenediamine and 0.012% of $H_2O_2$. Alternatively to this, o-phenylenediamine can be employed in a buffer (pH 5) which contains $Na_3PO_4$ and citric acid. The color development was stopped using 1 N $H_2SO_4$ (0.05 ml/well). The absorption for each well was measured at 492–405 nm and the data were evaluated by standard methods.

The test for inhibition of GP IIb/IIIa ("Fibrinogen-GP $II_bIII_a$ Receptor ELISA Binding Assay") was carried out as described in U.S. Pat. No. 5,403,836 which is incorporated herein by reference (the test method is abbreviated as "GP IIb/IIa" in the listing of the test results).

The following test results (inhibitory concentrations $IC_{50}$) were obtained.

| Compound | K/VnR $IC_{50}$ (nM) | GP IIb/IIIa $IC_{50}$ (nM) |
|---|---|---|
| Example 1 | 7.5 | 260 |
| Example 2 | 2.7 | 525 |
| Example 3 | 3.0 | 765 |
| Example 4 | 2.8 | 410 |
| Example 5 | 3.5 | 3150 |
| Example 6 | 2.8 | 720 |
| Example 7 | 3.5 | 950 |
| Example 8 | 2.5 | 330 |
| Example 9 | 5.3 | 2100 |
| Example 10 | 7.6 | 2400 |

European Patent Application 99102916.6, filed Feb. 13, 1999, is hereby incorporated by reference in its entirety.

What is claimed is:

1. A compound of the formula I

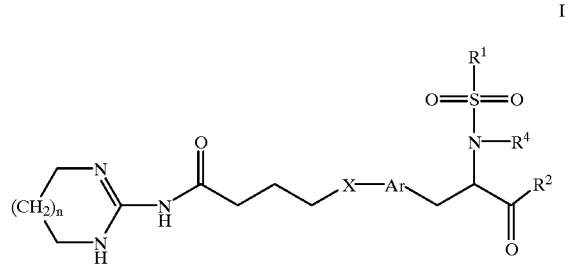

in which $R^1$ is $(C_1-C_{20})$-alkyl, $(C_3-C_{16})$-cycloalkyl, $(C_3-C_{16})$-cycloalkyl-$(C_1-C_6)$-alkyl-, $(C_6-C_{14})$-aryl, $(C_6-C_{14})$-aryl-$(C_1-C_6)$-alkyl-, $(C_5-C_{14})$-heteroaryl or $(C_5-C_{14})$-heteroaryl-$(C_1-C_6)$-alkyl-, where the alkyl residue, the cycloalkyl residue, the aryl residue and the heteroaryl residue each is unsubstituted or is substituted by one, two or three identical or different residues $R^3$, and where in the alkyl residue and the cycloalkyl residue one, two or three $CH_2$ groups can be replaced by identical or different groups selected from the series consisting of O, S and $NR^4$;

$R^2$ is hydroxy, amino, $(C_1-C_6)$-alkoxy, $(C_1-C_6)$-alkyl-CO—O—$(C_1-C_4)$-alkoxy-, $(C_3-C_{16})$-cycloalkyloxy, $(C_3-C_{16})$-cycloalkyl-CO—O—$(C_1-C_4)$-alkoxy- or $(C_6-C_{14})$-aryl-CO—O—$(C_1-C_4)$-alkoxy-, where the alkoxy residue, the alkyl residue, the aryl residue and the cycloalkyl residue each is unsubstituted or is substituted by one, two or three identical or different residues from the group consisting of hydroxy, halogen, oxo, CN, $(C_1-C_4)$-alkyl-CO—, $(C_1-C_4)$-alkyl-CO—NH—, $H_2N$—CO—, $(C_1-C_4)$-alkyl-NH—CO—, COOH, —CO—O—$(C_1-C_4)$-alkyl, $(C_1-C_4)$-alkyl, $(C_1-C_4)$-alkoxy, $(C_1-C_4)$-alkyl-$S(O)_2$—, —$NR^7R^{7'}$ and —$N^+R^7R^{7'}R^{7''}$ Q$^-$, where $R^7$, $R^{7'}$ and $R^{7''}$ independently of one another are hydrogen, $(C_1-C_6)$-alkyl, $(C_5-C_{14})$-aryl or $(C_5-C_{14})$-aryl-$(C_1-C_6)$-alkyl- and Q$^-$ is a physiologically tolerable anion, or $R^2$ is an amino acid residue which is bonded to the CO group carrying the group $R^2$ through an amino group;

$R^3$ is $(C_1-C_8)$-alkyl, $(C_3-C_{12})$-cycloalkyl, $(C_1-C_8)$-alkoxy, $(C_6-C_{14})$-aryl, $(C_6-C_{14})$-aryl-$(C_1-C_4)$-alkyl-, halogen, trifluoromethyl, cyano, hydroxy, oxo, nitro, amino, $(C_1-C_4)$-alkyl-$S(O)_2$—, —NH—$(C_1-C_4)$-alkyl, —N$((C_1-C_4)$-alkyl$)_2$, —NH—CO—$(C_1-C_4)$-alkyl, —CO—$(C_1-C_4)$-alkyl, —CO—NH$_2$, —CO—NH—$(C_1-C_4)$-alkyl, —COOH or —CO—O—$(C_1-C_4)$-alkyl;

$R^4$ is hydrogen or $(C_1-C_8)$-alkyl;

Ar is a 6-membered monocyclic aromatic ring system containing 0, 1, 2, 3, or 4 ring nitrogen atoms which is unsubstituted or substituted with one or more identical or different residues $R^3$;

X is CH$_2$, O, NR$^4$ or S;

n is zero, one or two;

in all its stereoisomeric forms and mixtures thereof in all ratios, and its physiologically tolerable salts.

2. A compound of the formula I as claimed in claim 1, in which $R^1$ is $(C_1-C_{10})$-alkyl, $(C_3-C_{12})$-cycloalkyl, $(C_3-C_{12})$-cycloalkyl-$(C_1-C_6)$-alkyl-, $(C_6-C_{14})$-aryl, $(C_6-C_{14})$-aryl-$(C_1-C_6)$-alkyl-, $(C_5-C_{14})$-heteroaryl or $(C_5-C_{14})$-heteroaryl-$(C_1-C_6)$-alkyl-, where the alkyl residue, the cycloalkyl residue, the aryl residue and the heteroaryl residue each is unsubstituted or is substituted by one, two or three identical or different residues $R^3$, and where in the alkyl residue and the cycloalkyl residue one, two or three CH$_2$ groups can be replaced by identical or different groups selected from the series consisting of O, S and NR$^4$;

$R^2$ is hydroxy, amino, $(C_1-C_6)$-alkoxy or $(C_1-C_6)$-alkyl-CO—O—$(C_1-C_4)$-alkoxy-, where the alkoxy residue and the alkyl residue each is unsubstituted or is substituted by one, two or three identical or different residues from the group consisting of hydroxy and halogen;

$R^3$ is $(C_1-C_6)$-alkyl, $(C_3-C_{12})$-cycloalkyl, $(C_1-C_6)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is CH$_2$ or O;

n is one;

in all its stereoisomeric forms and mixtures thereof in all ratios, and its physiologically tolerable salts.

3. A compound of the formula I as claimed in claim 1, in which $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one, two or three identical or different residues $R^3$;

$R^2$ is hydroxy or $(C_1-C_6)$-alkoxy, where the alkoxy residue is unsubstituted or is substituted by one, two or three identical or different residues from the group consisting of hydroxy and halogen;

$R^3$ is $(C_1-C_4)$-alkyl, $(C_3-C_{12})$-cycloalkyl, $(C_1-C_4)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is CH$_2$ or O;

n is one;

in all its stereoisomeric forms and mixtures thereof in all ratios, and its physiologically tolerable salts.

4. A compound of the formula I as claimed in claim 1, in which $R^1$ is $(C_1-C_{10})$-alkyl, $(C_3-C_{12})$-cycloalkyl, $(C_3-C_{12})$-cycloalkyl-$(C_1-C_4)$-alkyl-, $(C_6-C_{14})$-aryl, $(C_6-C_{14})$-aryl-$(C_1-C_4)$-alkyl-, $(C_5-C_{14})$-heteroaryl or $(C_5-C_{14})$-heteroaryl-$(C_1-C_4)$-alkyl-, where the alkyl residue, the cycloalkyl residue, the aryl residue and the heteroaryl residue each is unsubstituted or is substituted by one or two identical or different residues $R^3$;

$R^2$ is hydroxy or $(C_1-C_6)$-alkoxy;

$R^3$ is $(C_1-C_4)$-alkyl, $(C_1-C_4)$-alkoxy, $(C_6-C_{14})$-aryl, $(C_6-C_{14})$-aryl-$(C_1-C_4)$-alkyl-, halogen or trifluoromethyl;

$R^4$ is hydrogen;

the divalent residue —Ar— is 1,4-phenylene;

X is O;

n is one;

in all its stereoisomeric forms and mixtures thereof in all ratios, and its physiologically tolerable salts.

5. A compound of the formula I as claimed in claim 1, which is a 2-($R^1$-sulfonylamino)-3-(4-(3-(1,4,5,6-tetrahydropyrimidin-2-ylcarbamoyl)-propoxy)-phenyl)-propionic acid wherein the 2-($R^1$-sulfonylamino) substituent is selected from the group consisting of benzenesulfonylamino, toluene-4-sulfonylamino, 4-chlorobenzenesulfonylamino, 4-bromobenzenesulfonylamino, 4-trifluoromethylbenzenesulfonylamino, naphthalene-1-sulfonylamino, naphthalene-2-sulfonylamino, thiophene-2-sulfonylamino, butane-1-sulfonylamino and octane-1-sulfonylamino, in all its stereoisomeric forms and mixtures thereof in all ratios, and its physiologically tolerable salts.

6. A process for the preparation of a compound as claimed in claim 1, comprising reacting a carboxylic acid or a carboxylic acid derivative of the formula II

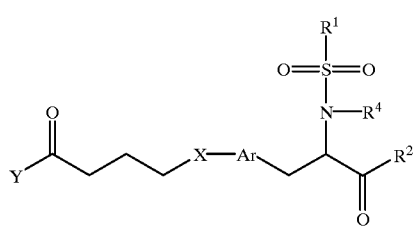

II in which $R^1$, $R^2$, $R^4$, Ar and X are defined as indicated in claim 1, or in which alternatively functional groups are present in the form of precursors which are later converted into the groups present in the compounds of the formula I, or in which functional groups are present in protected form, and in which Y is a nucleophilically substitutable leaving group, with a guanidine of the formula III

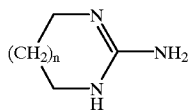    III in which n is defined as indicated in claim 1.

7. A pharmaceutical preparation, comprising at least one compound of the formula I as claimed in claim 1 and/or its physiologically tolerable salts and a pharmaceutically acceptable carrier.

8. A method for inhibiting binding of a vitronectin receptor, comprising contacting a compound of formula I as claimed in claim 1 and/or its physiologically tolerable salts with one or more vitronectin receptors.

9. A method for inhibiting bone resorption, osteoporosis, tumor growth or tumor metastasis, inflammation, or for the treatment of cardiovascular disorders, restenosis, arteriosclerosis, nephropathies, retinopathies or rheumatoid arthritis, comprising administering an effective dose of a compound of the formula I as claimed in claim 1 and/or its physiologically tolerable salts to an individual in need thereof.

10. A method of inhibiting binding of a vitronectin receptor comprising administering an effective dose of a compound of formula I as claimed in claim 1 and/or its physiologically tolerable salts to an individual in need thereof.

* * * * *